(12) United States Patent
Whalen, II et al.

(10) Patent No.: US 7,083,643 B2
(45) Date of Patent: *Aug. 1, 2006

(54) METHODS FOR TREATING ANEURYSMS

(75) Inventors: Thomas J. Whalen, II, Encinitas, CA (US); Richard J. Greff, St. Pete Beach, FL (US); Kevin P. Gilmartin, Carlsbad, CA (US); Douglas Ray Hayman, Mission Viejo, CA (US); Todd J. Hewitt, Laguna Niguel, CA (US); Ed L. Olson, Lake Forest, CA (US); Mark A. Pecor, Mission Viejo, CA (US); Earl H. Slee, Laguna Niguel, CA (US); George Wallace, Coto De Caza, CA (US)

(73) Assignee: Micro Therapeutics, Inc., Irvine, CA (US)

( * ) Notice: Subject to any disclaimer, the term of this patent is extended or adjusted under 35 U.S.C. 154(b) by 311 days.

This patent is subject to a terminal disclaimer.

(21) Appl. No.: 10/388,741

(22) Filed: Mar. 17, 2003

(65) Prior Publication Data

US 2003/0135264 A1    Jul. 17, 2003

Related U.S. Application Data

(63) Continuation of application No. 09/811,423, filed on Mar. 20, 2001, now Pat. No. 6,569,190.

(60) Provisional application No. 60/239,777, filed on Oct. 11, 2000.

(51) Int. Cl.
*A61F 2/06* (2006.01)

(52) U.S. Cl. .................. 623/1.42; 623/903; 606/200

(58) Field of Classification Search ...... 623/1.11–1.15, 623/1.42–1.48, 903; 606/49–53, 200, 57; 604/508

See application file for complete search history.

(56) References Cited

U.S. PATENT DOCUMENTS

| | | |
|---|---|---|
| 3,527,224 A | 9/1970 | Rabinowitz et al. |
| 3,591,676 A | 7/1971 | Hawkins et al. |
| 4,938,763 A | 7/1990 | Dunn et al. |
| 5,213,580 A | 5/1993 | Slepian et al. |
| 5,421,826 A | 6/1995 | Crocker et al. |
| 5,458,568 A | 10/1995 | Racchini et al. |

(Continued)

OTHER PUBLICATIONS

Aletich, et al., "The Remodeling Technique of Balloon-Assisted Guglielmi Detachable Coil Placement in Wide-Necked Anuerysms: Experience at the University of Illinois at Chicago", *J. Neurosurg*, 93: 388-396 (2000).

(Continued)

*Primary Examiner*—Suzette J-J Gherbi
(74) *Attorney, Agent, or Firm*—Foley & Lardner LLP

(57) ABSTRACT

This invention is directed to methods for treating aneurysms wherein the aneurysmal sac is filled with a non-particulate agent or plurality of such agents and/or with a fluid composition which solidifies in situ. Filling of the aneurysmal sac employs sufficient amount of the non-particulate agent or plurality of such agents and/or the fluid composition to inhibit blood flow into the aneurysm sac. In addition, the methods of this invention also provide for non-endogenous isolation of the parent artery proximal and distal to the aneurysmal sac from systemic blood flow of the treated mammal. The combination of these features provides for treatment of the aneurysmal sac while, at the same time, inhibiting aneurysm formation and/or regrowth in the diseased portions of the arterial wall proximal and distal to the treated aneurysm.

5 Claims, 2 Drawing Sheets

U.S. PATENT DOCUMENTS

| | | | |
|---|---|---|---|
| 5,542,926 A | 8/1996 | Crocker | |
| 5,569,184 A | 10/1996 | Crocker et al. | |
| 5,575,815 A | 11/1996 | Slepian et al. | |
| 5,580,568 A | 12/1996 | Greff et al. | |
| 5,634,946 A | 6/1997 | Slepian | |
| 5,650,447 A | 7/1997 | Keefer et al. | |
| 5,667,767 A | 9/1997 | Greff et al. | |
| 5,674,287 A | 10/1997 | Slepian et al. | |
| 5,695,480 A | 12/1997 | Evans et al. | |
| 5,702,361 A * | 12/1997 | Evans et al. | 604/508 |
| 5,749,915 A | 5/1998 | Slepian | |
| 5,749,922 A | 5/1998 | Slepian et al. | |
| 5,800,538 A | 9/1998 | Slepian et al. | |
| 5,830,178 A | 11/1998 | Jones et al. | |
| 5,843,156 A | 12/1998 | Slepian et al. | |
| 5,855,563 A | 1/1999 | Kaplan et al. | |
| 5,888,546 A | 3/1999 | Ji et al. | |
| 5,894,022 A | 4/1999 | Ji et al. | |
| 5,914,345 A | 6/1999 | Slepian et al. | |
| 5,921,954 A | 7/1999 | Mohr, Jr. et al. | |
| 5,947,977 A | 9/1999 | Slepian et al. | |
| 5,951,599 A * | 9/1999 | McCrory | 606/108 |
| RE36,370 E | 11/1999 | Li | |
| 6,007,573 A | 12/1999 | Wallace et al. | |
| 6,007,833 A | 12/1999 | Chudzik et al. | |
| 6,017,977 A | 1/2000 | Evans et al. | |
| 6,096,021 A | 8/2000 | Helm et al. | |
| 6,241,719 B1 | 6/2001 | Wallace et al. | |
| 6,254,628 B1 * | 7/2001 | Wallace et al. | 623/1.12 |
| 6,335,384 B1 * | 1/2002 | Evans et al. | 523/113 |
| 6,344,048 B1 * | 2/2002 | Chin et al. | 606/200 |

OTHER PUBLICATIONS

"CANCER, Principles & Practice of Oncology", 4th Ed., vol. 1, "Cancer Treatment", pp. 545-548 (1993).

Castaneda-Zuniga, et al., *Interventional Radiology*, in Vascular Embolotherapy, Part 1, 1:9-32, Williams & Wilkins, Publishers (1992).

Cognard, et al., "Treatment of Distal Aneurysms of the Cerebellar Arteries by Intraaneurysmal Injection of Glue", *Am. J. Neuroradiol.*, 20: 780-784 (1999).

Fischell, et al., "The Beta-Particle-Emitting Radioisotope Stent (Isostent): Animal Studies and Planned Clinical Trials", *Am. J. Cardiol.*, 78(suppl 3A): 45-50 (1996).

Fischell, et al., "Low-Dose, β-Particle Emission From "Stent" Wire Results in Complete, Localized Inhibition of Smooth Muscle Cell Proliferation", *Circulation*, 90(6): 2956-2963 (1994).

Hill-West, et al., "Inhibition of Thrombosis and Intimal Thickening by *in situ* Photopolymerization of Thin Hydrogel Barriers", *Proc. Natl. Acad. Sci. USA*, 91: 5967-5971 (1994).

Geremia, et al., "Embolization of Experimentally Created Aneurysms with Intravascular Stent Devices", *AJNR*, 15: 1223-1231 (1994).

Gomez, et al., "Endovascular Theraphy of Traumatic Injuries of the Extracranial Cerebral Arteries", *Endovascular Therapy and Neurocritical Care* 15 (4): 789-809 (Oct. 1999).

Hemphili, III, et al., "Endovascular Therapy of Traumatic Injuries of the Intracranial Cerebral Arteries", *Endovascular Therapy and Neurocritical Care* 15 (4): 811-829 (Oct., 1999).

Jungreis, "The Use of Stents in Endovascular Intervention", *AJNR*, 16: 1976-1976 (1995).

Kinugasa, et al., "Direct Thrombosis of Aneurysms with Celluose Acetate Polymer", *J. Neurosurg.*, 77: 501-507 (1992).

Kinugasa, et al., "Early Treatment of Subarachnoid Hemorrhage After Preventing Rerupture of an Aneurysm", *J. Neurosurg.*, 83:34-41 (1995).

Kinugasa, et al., "Prophylactic Thrombosis to Prevent New Bleeding and to Delay Aneurysm Surgery", *Neurosurg.*, 36:661 (1995).

Kinugasa, et al., "Cellulose Acetate Polymer Thrombosis for the Emergency Treatment of Aneurysms: Angiographic Findings, Clinical Experience, and Histopathological Study", *Neurosurg.*, 34(4): 694-701 (1994).

Laird, et al., "Inhibition of Neointimal Proliferation With Low-Dose Irradiation From a β-Particle Emiting Stent," *Circulation* 93(3):529-536 (1996).

Malek, et al., "Balloon-assist Technique for Endovascular Coil Embolization of Geometrically Difficult Intracranial Aneurysm", *Neurosurgery*, 46(6): 1397-1407 (2000).

Mandai, et al., "Direct Thrombosis of Aneurysms with Cellulose Acetate Polymer: Part I—Results of Thrombosis in Experimental Aneurysms", *J. Neurosurg.*, 77: 497-500 (1992).

Mericle, et al., "Stenting and Secondary Coiling of Intracranial Internal Carotid Artery Aneurysm: Technical Case Report", *Neurosurgery*, 43(5): 1229-1234 (1998).

Moret, et al., "The "Remodeling Technique" in the Treatment of Wide Neck Intracranial Aneurysms", *Interventional Neuroradiology*, 3: 21-35 (1997).

Nelson, et al., "Balloon-assisted Coil Embolization of Wide-Necked Aneurysms of the Internal Carotid Artery: Medium-term Angiographic and Clinical Follow-up in 22 Patients", *Am J. Neuroradiol.*, 22: 19-26 (2001).

Pierot, et al., "Endovascular Treatment of Post-Traumatic Complex Carotid-Cavernous Fistulas, Using the Arterial Approach", *J. Neuroradiol.*, 19: 79-87 (1992) (document presented in both English and French).

Popowski, et al., "Intra-Arterial $^{90}$Y Brachytherapy: Preliminary Dosimetric Study Using a Specially Modified Angioplasty Balloon", *Int. J. Radiation Oncology Biol. Phys.*, 33(3): 713-717 (1995).

Riina, et al. "Future Endovascular Management of Cerebral Aneurysms", *Neurosurgery Clinics of North America*, 9(4): 917-921 (1998).

Schopohl, et al., "$^{192}$IR Endovascular Brachytherapy for Avoidance of Intimal Hyperplasia After Percutaneous Transluminal Angioplasty and Stent Implantation in Peripheral Vessels: 6 Years of Experience", *Int. J. Radiation Oncology Biol. Phys.*, 36(4): 835-840 (1996).

Slepian, "Polymeric Endoluminal Paving: A Family of Evolving Methods for Extending Endoluminal Therapeutics Beyond Stenting", *Contemporary Interventional Techniques* 12 (4): 715-737 (1994).

Slepian, et al. "Polymeric Endoluminal Gel Paving: Therapeutic Hydrogel Barriers and Sustained Drug Delivery Depots for Local Arterial Wall Biomanipulation." *Semin. Intervent. Cardiol.* 1: 103-116 (1996). (Article not enclosed herewith. Applicant will provide a copy as soon as possible after filing this IDS).

Slepian, et al., "$β_3$-Integrins Rather than $β_1$-Integrins Dominate Integrin-Matrix Interactions involved in Postinjury Smooth Muscle Cell Migration", *American Heart Association*, pp. 1818-1827, May 12, 1998.

Slepian, et al., "Pre-Conditioning of Smooth Muscle Cells via Induction of the Heat Shock Response Limits Proliferation Following Mechanical Injury", *Biochemical and Biophysical Research Communications*, 225: 600-607 (1996) (Article No. 1217).

Szikora, et al., "Endovascular Treatment of Experimental Aneurysms with Liquid Polymers: The Protective Potential of Stents", *Neurosurgery*, 38 (2): 339-347 (1996).

Taki, et al., "Selection and Combination of Various Endovascular Techniques in the Treatment of Giant Aneurysms", *J. Neurosurg.*, 77:37-24 (1992).

Talja, et al., "Bioabsorbable and Biodegradable Stents in Urology", *Journal of Endourology*, 11(6): 391-397 (1997).

Violaris, et al., "Endovascular Stents: a "Break Through Technology", Future Challenges", *International Journal of Cardiac Imaging*, 13: 3-13 (1997).

Waksman, et al., "Local Catheter-Based Intracoronary Radiation Therapy for Restenosis", *Am. J. Cardiol.*, 78 (suppl 3A): 23-28 (1996).

Weill, et al., "Giant Aneurysms of the Middle Cerebral Artery Trifurcation Treated with Extracranial-Intracranial Arterial Bypass and Endovascular Occlusion", *J. Neurosurg.*, 89: 474-478 (1998).

* cited by examiner

METHODS FOR TREATING ANEURYSMS

CROSS REFERENCE TO RELATED APPLICATION

This application is a continuation of application Ser. No. 09/811,423, filed on Mar. 20, 2001, now U.S. Pat. No. 6,569,190, which claims priority to U.S. Provisional Patent Application Ser. No. 60/239,777, filed Oct. 11, 2000, both of which are incorporated herein in their entirety.

BACKGROUND OF THE INVENTION

1. Field of the Invention

This invention is directed to methods for treating aneurysms in a mammalian patient.

REFERENCES

The following publications are cited in this application as superscript numbers:

1. Castaneda-Zuniga, et al., *Interventional Radiology*, in Vascular Embolotherapy, Part 1, 1:9–32, Williams & Wilkins, Publishers (1992)
2. Greff, et al., Compositions for Use in Embolizing Blood Vessels, U.S. Pat. No. 5,667,767, issued Sep. 16, 1997
3. Evans, et al., Cellulose Diacetate Compositions for Use in Embolizing Blood Vessels,. U.S. Pat. No. 5,580,568, issued Dec. 3, 1996
4. Evans, et al., Novel Embolizing Compositions, U.S. Pat. No. 5,695,480, issued Dec. 9, 1997
5. Jones, et al., Methods for Embolizing Vascular Sites with an Embolizing Composition Comprising Dimethylsulfoxide, U.S. Pat. No. 5,830,178, issued Nov. 3, 1998
6. Whalen, et al., Novel Embolizing Compositions Comprising High Polymer Concentrations, U.S. patent application Ser. No. 09/574,379, filed May 19, 2000
7. Evans, et al., Methods for Embolizing Blood Vessels, U.S. Pat. No. 5,702,361, issued Dec. 30, 1997
8. Evans, et al., Methods for Embolizing Blood Vessels, U.S. Pat. No. 6,017,977, issued Jan. 25, 2000
9. Wallace, et al., Intracranial Stent and Method of Use, U.S. Pat. No. 6,007,573, issued Dec. 28, 1999.
10. Racchini, et al., Porous Balloon For Selective Dilation and Drug Delivery, U.S. Pat. No. 5,458,568, issued Oct. 17, 1995
11. Whalen, et al., Novel High Viscosity Embolizing Compositions, U.S. patent application Ser. No. 09/574,379, May 19, 2000
12. Szikora, et al., *Endovascular Treatment of Experimental Aneurysms with Liquid Polymers: The Protective Potential of Stents*, Neurosurgery, 38(2):339–347 (1996)
13. Kinugasa, et al., *Direct Thrombosis of Aneurysms with Cellulose Acetate Polymer, Part II - Preliminary Clinical Experience*, J. Neurosurg., 77:501–507 (1992)
14. Kinugasa, et al., *Cellulose Acetate Polymer Thrombosis for the emergency Treatment of Aneurysms: Angiographic Finding, Clinical Experience, and Histopathological Study*, Neurosurgery, 34:694–701 (1994)
15. Mandai, et al., *Direct Thrombosis of Aneurysms with Cellulose Acetate Polymer: Part I—Results of Thrombosis in Experimental Aneurysms*, J. Neurosurg., 77:497–500 (1992)
16. Talia, et al., *Bioabsorbable and Biodegradable Stents in Urology*, J. Endourology, 11(6):391 (1997)
17. Wallace, et al., Intracranial Stent, U.S. Pat. No. 6,254,628 issued Jul. 3, 2001.
18. Dunn, et al., U.S. Pat. No. 4,938,763 for "Biodegradable In-Situ Forming Implants and Methods for Producing Same" issued Jul. 3, 1990.
19. "CANCER, Principles & Practice of Oncology", 4th Ed., Volume 1, "Cancer Treatment", pp. 545–548 (1993).

All of the above references are herein incorporated by reference in their entirety to the same extent as if each individual reference was specifically and individually indicated to be incorporated herein by reference in its entirety.

2. State of the Art

Aneurysms arise in mammalian subjects and, in particular, human subjects as a result of vascular disease wherein the arterial (wall) weakens and, under pressure due to blood flow, the arterial wall "balloons". Continued growth and/or eventual rupture of the ballooned arterial wall is associated with high morbidity and mortality rates. Intracranial aneurysms are of particular concern because surgical procedures to treat these aneurysms before rupture are often not feasible and further because rupture of these aneurysms can have devastating results on the patient even if the patient survives rupture. Accordingly, treatment protocols for intracranial aneurysms may be prophylactic in nature, i.e., to inhibit rupture or rerupture of the aneurysm rather than to inhibit bleeding from the ruptured aneurysm.

Methods well documented in the art to inhibit intracranial aneurysmal rupture include the delivery into the aneurysmal sac of non-particulate agents such as metal coils which are designed to induce thrombosis after delivery to the aneurysm thereby inhibiting blood flow into the aneurysm[1]; delivery of a fluid composition into the aneurysmal sac which composition solidifies in the sac to inhibit blood flow into the aneurysm[2-6]; or a delivery of a combination of non-particulate agents and a fluidic composition into the aneursymal sac to inhibit blood flow into the aneurysm.[7-8]

In each case, the cranial aneurysm is treated by filling the aneurysmal sac in a manner which inhibits blood flow into the sac. This reduced blood flow correlates to reductions in aneurysmal pressure and, hence, a reduction in the likelihood of rupture. However, care must be taken to ensure against migration of non-particulate agents or fluid composition beyond the aneurysmal sac (which can occur, for example, by overfilling of the sac) because this can result in parent artery or distal embolization which, in turn, has its own high level of morbidity associated therewith.[12]

Notwithstanding the benefits that these methods provide in inhibiting aneurysmal rupture, in a significant number of cases, the treatment protocol is only effective for a short period of time due to reformation of the aneurysmal sac or formation of a new aneurysmal sac at or adjacent the previously treated aneurysm in the treated patient.[13-15]

Upon careful analysis, this invention is based upon the discovery that subsequent re-treatment arising after initial treatment of the aneurysm by filling the aneurysmal sac with non-particulate agents and/or fluidic compositions was necessitated because the initial treatment did not address all of the diseased tissue. Specifically, the aneurysmal sac in the parent artery often reflects only the most diseased and hence weakest portion of the arterial wall. However, regions proximal and distal to the aneurysmal sac are often diseased and prone to ballooning. Hence, when the aneurysmal sac is filled via the methods described above, other diseased portions of the arterial wall adjacent to the treated aneurysm become more likely to balloon and rupture. It is this latter phenomena that is believed to result in retreatment of the aneurysm.

While Szikora, et al.[12] discloses the use of a porous stent in combination with a fluid composition in treating an aneurysm, the stent employed is a porous stent and the amount of polymer employed is less than that necessary to completely fill the aneurysmal sac. Accordingly, the techniques disclosed therein do not isolate the parent artery proximal and distal to the aneurysmal sac from blood flow.

SUMMARY OF THE INVENTION

This invention is directed to methods for treating aneurysms wherein the aneurysmal sac is filled with a non-particulate agent or plurality of such agents and/or with a fluid composition which solidifies in situ. Filling of the aneurysmal sac employs sufficient amount of the non-particulate agent or plurality of such agents and/or the fluid composition to inhibit blood flow into the aneurysm sac. In addition, the methods of this invention also provide for non-endogenous isolation of the parent artery proximal and distal to the aneurysmal sac from systemic blood flow of the treated mammal. The combination of these features provides for treatment of the aneurysmal sac while, at the same time, inhibiting aneurysm formation and/or regrowth in the diseased portions of the arterial wall proximal and distal to the treated aneurysm.

Preferably, the aneurysm treated is an intracranial (cerebral) aneurysm.

Accordingly, in one of its method aspects, this invention is directed to a method for treating an aneurysm in a mammalian patient which method comprises:
  (a) identifying the vascular site of an aneurysm in a mammalian patient wherein said aneurysm comprises an aneursymal sac formed from the vascular wall of a parent artery and further wherein said aneurysmal sac participates in the systemic blood flow of said patient;
  (b) inhibiting systemic blood flow into said aneurysmal sac by filling at least a portion of said sac with a fluid composition and/or a non-particulate agent or plurality of said agents; and
  (c) non-endogenously isolating the parent artery proximal and distal to said aneurysm from systemic blood flow.

In the methods described above, the non-particulate agents preferably comprise metallic coils and, more preferably, platinum coils.

The fluid composition employed in the methods of this invention preferably comprises either a biocompatible polymer or a biocompatible prepolymer. When a biocompatible polymer is employed, the fluid composition preferably comprises a biocompatible polymer, a biocompatible contrast agent, and a biocompatible solvent which solubilizes the biocompatible polymer wherein sufficient amounts of the polymer are employed in the composition such that, upon delivery to the aneurysm, a polymer precipitate forms which fills at least a portion of the aneurysmal sac thereby inhibiting blood flow therein. Preferably, the viscosity of the polymer composition is at least about 150 cSt at 40° C.

Such polymer composition can comprise, for example, a biocompatible polymer at a concentration of from about 2 to 50 weight percent; a biocompatible contrast agent at a concentration of from about 10 to about 40 weight percent; and a biocompatible solvent from about 10 to 88 weight percent wherein the weight percent of the biocompatible polymer, contrast agent and biocompatible solvent is based on the total weight of the complete composition.

Preferably, in this particular composition, the concentration of the polymer ranges from 6 to 50 weight percent and more preferably 8 to 30 weight percent.

Preferably, the polymer composition has a viscosity of at least about 150, preferably at least about 200 and more preferably at least 500 cSt at 40° C. More preferably the viscosity ranges from about 200 to 40,000 cSt at 40° C., more preferably from about 500 to 40,000 cSt at 40° C. In another embodiment, the viscosity ranges from about 500 to 5000 cSt at 40° C.

In another aspect of this invention, the biocompatible polymer can be replaced with a biocompatible prepolymer and, when so used, the presence of the biocompatible solvent becomes optional.

In a further preferred embodiment, the biocompatible solvent is dimethylsulfoxide (DMSO), ethanol, ethyl lactate or acetone.

Isolation of the parent artery proximal and distal to said aneurysm from systemic blood flow is preferably accomplished by placement of a stent adjacent the aneurysmal sac which stent extends in both the proximal and distal directions of the parent artery beyond the aneurysmal sac and isolates blood flow to the arterial walls of the parent artery overlayed by the stent. The stent employed can be either formed in situ or placed in the artery by microcatheter techniques.

Alternatively, the use of novel balloon catheters allow for the use of fluid compositions to form a coherent precipitate in the aneurysmal sac and which extends from the neck of the sac both distally and proximally to both fill the aneurysmal sac and to isolate the parent artery from the systemic blood flow both distally and proximally from the site of the aneurysm.

In either case, the methods of this invention entail the non-endogenous isolation of the parent artery wall to the systemic blood flow both proximal and distal to the site of the aneurysmal sac. The parent artery is isolated either immediately adjacent the aneurysmal sac or around the entire inner circumference of the parent artery. The parent artery is preferably isolated by at least about 2 to 10 mm proximal and distal to said aneurysm from systemic blood flow and more preferably by no more than about 3 to 5 mm proximal and distal to said aneurysm.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE INVENTION

Figure 1:
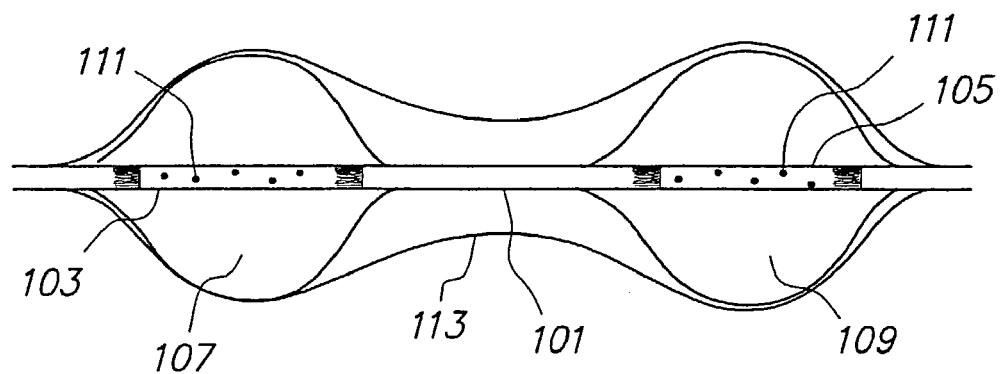
FIG. 1 is a schematic side view of a balloon catheter for use in a method of treating an aneurysm according to one embodiment of the invention.

This invention is directed to methods for treating aneurysms in mammals. However, prior to discussing this invention in further detail, the following terms will first be defined:

The term "biocompatible polymer" refers to polymers which, in the amounts employed, are non-toxic and substantially non-immunogenic when used internally in the patient and which are substantially insoluble in the body fluid of the mammal.

The biocompatible polymer is preferably non-biodegradable. Suitable non-biodegradable biocompatible polymers include, by way of example, cellulose acetates[2-6] (including cellulose diacetate), ethylene vinyl alcohol copolymers, hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof.

Biodegradable polymers are disclosed in the art.[18, 19] For example, Dunn, et al.18 discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosa, and copolymers, terpolymers and combinations thereof. Other biodegradable polymers include, for example, fibrin, gelatin, collagen, etc.

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by, e.g., injection. Such factors are well within the skill of the art.

Delivery means such as the threaded syringes described, for example, in U.S. Provisional Patent Application Serial Nos. 60/135,289 and 60/135,287, entitled "THREADED SYRINGE" under Attorney Docket No. 018413-194 and entitled "SCREW SYRINGE WITH FORCE RELEASE MECHANISM" under Attorney Docket No. 018413-198, both of which were filed on May 21, 1999 can be used to assist in delivery of the fluid composition to the vascular site of the aneurysm, particularly where compositions with high viscosities are used. Both of these applications are incorporated herein by reference in their entirety.

Preferred biocompatible polymers include cellulose diacetate and ethylene vinyl alcohol copolymer.

Cellulose diacetate polymers are either commercially available or can be prepared by art recognized procedures.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

The term "contrast agent" refers to a biocompatible radiopaque material capable of being monitored during injection into a mammalian subject by, for example, radiography. The contrast agent can be either water soluble or water insoluble and preferably does not contain radioactivity above the native or endogenous amounts naturally occurring in the elements employed (i.e., are "non-radioactive").

Examples of water soluble contrast agents include metrizamide, iopamidol, iothalamate sodium, iohexol, iodomide sodium, and meglumine. Examples of water insoluble contrast agents include tantalum, tantalum oxide, and barium sulfate, each of which is commercially available in the proper form for in vivo use including a preferred particle size of about 10 μm or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, ethyl lactate, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic and substantially non-immunogenic when used internally in the patient and which are substantially insoluble in blood. Suitable biocompatible prepolymers include, by way of example, urethanes, cyanoacrylates, (C1–C6)hydroxyalkyl (C1–C6)alkacrylate (e.g., hydroxyethyl methacrylate), silicone prepolymers, and the like. The prepolymer can either be a monomer or a reactive oligomer. Preferably, the biocompatible prepolymer does not cause an adverse inflammatory reaction when employed in vivo.

A "stent" is a device which retains integrity of the vascular wall when it is placed in contact with or when it is formed in situ adjacent to or in contact with a vascular wall. A stent functions to maintain patency of a body lumen (such as a vascular wall) and is especially used as an implant in blood vessels. Stents may be used after angioplasty to prevent acute re-closure of the blood vessel afterwards. Stents may be utilized after atherectomy, which excises plaque, or cutting balloon angioplasty, which scores the arterial wall prior to dilatation, to maintain acute and long-term patency of the vessel. Stents may be utilized in by-pass grafts as well, to maintain vessel patency. Effectively, a stent overcomes the natural tendency of the vessel walls of some patients to close back down, thereby maintaining a more normal flow of blood through that vessel than would otherwise be possible if the stent were not in place.

Suitable stents include open, lattice or porous stents in which the structure of the stent is mesh-like in nature having one or more openings or pores. The size of at least one of the openings in the stent is preferably large enough to permit a catheter to pass through the stent. Openings of about 0.1 mm to about 10 mm are preferred for traversal of the catheter through the opening. Openings of about 1.0 mm to about 10 mm are still more preferred for traversal of the catheter through the opening.

Alternatively, stents having one or more grooves (e.g., chevrons) on the surface such that there are cavities created between the stent and the arterial wall can also be employed in the methods of this inventions.

A "liquid permeable balloon" is a balloon which comprises at least a portion of a permeable balloon membrane which membrane allows the passage, under positive pressure, of a composition comprising a liquid composition such as a biocompatible polymer or prepolymer, a biocompatible'solvent and a contrast agent. The permeable balloon membrane is preferably selected to allow the passage of insoluble particles having a particle size no larger than 10 µm. The positive pressure employed is preferably at least 5 atmospheres, more preferably 5 to 75 atmospheres, still more preferably 10 to 50 atmospheres, and further more preferably 5 to 30 atmospheres, and still further more preferably 5 to 20 atmospheres. The permeable material employed in the balloon is not critical provided that it meets the above criteria. Such materials include, by way of example, expanded polytetrafluoroethylene (PTFE, tradename Gortex™), polyethyleneterephthalate (Dacron™, DuPont, Wilmington, Del.), and polyethylene with laser drilled openings. Liquid permeable balloons are also described by Racchini, et al.[10]

The term "non-particulate agent" refers to biocompatible macroscopic solid materials having a discrete physical shape or structure which, when placed in a blood vessel, result in embolization of the blood vessel. The non-particulate agents are macroscopic (i.e., about 1 mm or larger in size) which is contrasted with particulates which are microscopic (i.e., less than 1 mm in size). Examples of such non-particulate agents include, coils (including metallic coils, coils with barbs, etc.), silk streamers, plastic brushes, detachable balloons (e.g., silicon or latex balloons), foam (e.g., polyvinyl alcohol foam), nylon mesh and the like. Such non-particulate agents are generally commercially available. For example, platinum coils are available from Boston Scientific.

The specific non-particulate agent employed is not critical and preferred agents include metallic coils, metallic coils with barbs, metallic coils with fibers (e.g., Dacron® wool fibers) and/or streamers, etc. More preferably, platinum coils are employed.

"Parent artery" refers to the artery from which the aneurysm is formed.

"Aneurysms" refer to ballooning of the wall of an artery which, under continued pressure, leads to aneursym growth and/or arterial rupture. Included within this definition are aneurysms which have ruptured but sealed in vivo by, for example, thrombosis. As is apparent, bleeding ceases once the aneurysm has thrombosed.

"Non-endogenously isolating the parent artery" refers to procedures for isolating the arterial walls of the parent artery from systemic blood flow which procedures do not rely solely upon formation of biological tissue to effect complete isolation of the parent artery. In this regard, growth of endogenous tissue, e.g, over a porous stent, to isolate the parent artery from blood circulation often occurs weeks after placement of the stent during which time there can be regrowth of the aneurysmal sac or formation of a new aneurysm.

"Proximal" refers to the surface area of the arterial wall of the parent artery radially upstream of the aneurysmal sac, including arterial wall adjacent to or opposite the aneurysmal sac.

"Distal" refers to the surface area of the arterial wall of the parent artery radially downstream of the aneurysm sac, including arterial wall adjacent to or opposite to the aneurysmal sac.

"Solidification" refers to the in situ formation of a solid mass whether by the in situ polymerization of a prepolymer in the fluid composition or the precipitation of the polymer in the fluid composition.

Compositions

The polymer or prepolymer compositions employed in the methods of this invention are preferably first prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2 to about 50 weight percent of the biocompatible polymer composition based on the total weight of the polymer composition. If necessary, gentle heating and stirring can be used to effect dissolution of the biocompatible polymer into the biocompatible solvent, e.g., 12 hours at 50° C.

A sufficient amount of a contrast agent is then added to the composition to achieve the effective concentration for the complete composition. Preferably, the composition will comprise from about 5 to about 40 weight percent of contrast agent, and still more preferably 10 to 40 weight percent of contrast agent.

The biocompatible solvent preferably comprises from about 40 to about 90 weight percent of the composition based on the total weight of the composition and more preferably about 50 to about 90 weight percent.

When a water soluble contrast agent is employed, the agent is typically soluble in the solution comprising the non-aqueous solvent and stirring is effected to render the composition homogeneous.

When a water insoluble contrast agent is employed, the agent is insoluble in the biocompatible solvent, and stirring is employed to effect homogeneity,of the resulting suspension. In order to enhance formation of the suspension, the particle size of the water insoluble contrast agent is preferably maintained at about 10 µm or less and more preferably at from about 1 to about 5 µm (e.g., an average size of about 2 µm).

In one embodiment, a contrast agent having a particle size of less than 10 µm is prepared, for example, by fractionation. In such an embodiment, a water insoluble contrast agent such as tantalum, having an average particle size of less than about 20 µm, is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition can be heat sterilized and then stored preferably in sealed bottles or vials until needed.

Each of the polymers recited herein is commercially available or can be prepared by methods well known in the art. For example, polymers are typically prepared by conventional techniques such as radical, thermal, UV, γ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Further examples of suitable polymer compositions are disclosed by Whalen, et al.[11] and Evans, et al.[4]

Prepolymer compositions can be prepared by adding sufficient amounts of the contrast agent employed in the liquid (e.g., liquid prepolymer) to achieve the effective concentration for the complete prepolymer composition. Preferably, the contrast agent will comprise from about 5 to about 40 weight percent of the prepolymer composition based on the total weight of the composition.

When a contrast agent is used which is not soluble in the biocompatible prepolymer composition, stirring is employed to effect homogeneity of the resulting suspension. In order to enhance formation of the suspension, the particle size of the insoluble contrast agent is preferably maintained at about 10 μm or less and more preferably at from about 1 to about 5 μm (e.g., an average size of about 2 μm).

When the prepolymer is liquid (as in the case of cyanoacrylates or silicone), the use of a biocompatible solvent is not strictly necessary but may be preferred to provide for an appropriate viscosity, for an appropriate curing time, etc. in the composition. Preferably, when employed, the biocompatible solvent will comprise from about 30 to about 90 weight percent of the biocompatible prepolymer composition based on the total weight of the prepolymer composition, more preferably from about 60 to about 80 weight percent, and still more preferably from about 30 to 70. When a biocompatible solvent is employed, the prepolymeric composition typically comprises from about 10 to about 50 weight percent of the prepolymer based on the total weight of the composition, and more preferably from about 20 to about 60 weight percent.

Suitable solvents include iodinated soy bean or poppy seed oil for cyanoacrylates and water for hydroxyacrylics such as hydroxyethyl methacrylate. In such cases, the oil acts both as a carrier for the prepolymer, a contrast agent and a polymerization time modifier. Other solvents include hexamethyldisiloxane which is preferably employed in conjunction with silicone.

In a particularly preferred embodiment, the prepolymer is a cyanoacrylate which is preferably employed in a 1:1 ratio with an iodinated oil. When so employed, the cyanoacrylate adhesive is selected to have a viscosity of from about 5 to about 40 centipoise at 20° C.

Methods

This invention is based upon the discovery that subsequent re-treatment of the aneurysm arising after initial treatment of the aneurysm by filling the aneurysmal sac with non-particulate agents and/or fluidic compositions was necessitated because the initial treatment did not address all of the diseased tissue. Specifically, the aneurysmal sac in the parent artery often reflects only the most diseased and hence weakest portion of the arterial wall. However, regions proximal and distal to the aneurysmal sac are often diseased and prone to ballooning. Hence, when the aneurysmal sac is filled via the methods described above, other diseased portions of the arterial wall adjacent to the treated aneurysm become more likely to balloon and rupture. It is this latter phenomena that is believed to result in retreatment of the aneurysm.

The fluid compositions described above can then be employed in methods for the catheter assisted treatment of aneurysms in mammalian blood vessels and, in particular, in the treatment of intracranial aneurysms. In such methods, a sufficient amount of the fluid composition is introduced into the aneurysmal sac via a catheter delivery means under fluoroscopy so that upon solidification, the aneurysmal sac is sufficiently filled with a solid material to inhibit blood flow therein. Alternatively, the aneurysmal sac can be filled with a sufficient amount of a non-particulate agent or plurality of agents to inhibit blood flow therein. Still further, a combination of non-particulate agent/agents and a fluid composition can be employed to fill the aneurysmal sac.

These methods of delivering non-particulate agents, fluid compositions or a combination of both to the aneursymal sac to inhibit blood flow into the aneurysm are well known in the art.[1-8]

The particular amount of materials employed, as viewed by imaging (fluoroscopy), is dictated by the total volume of the aneurysmal sac, the level of filling, the concentration of polymer/prepolymer in the composition when a fluid composition is employed, the rate of precipitation (solids formation) of the polymer, etc. Such factors are well within the skill of the art.

The methods of this invention also entail the non-endogenous isolation of the parent artery wall to the systemic blood flow both proximal and distal to the site of the aneurysmal sac. The parent artery is isolated either immediately adjacent the aneurysmal sac or around the entire inner circumference of the parent artery. In this embodiment, the parent artery is preferably isolated by at least about 2 to 10 mm proximal and distal to said aneurysm from systemic blood flow and more preferably by no more than about 3 to 5 mm proximal and distal to said aneurysm.

One method for non-endogenously isolating the parent artery wall from the systemic blood flow is the formation of in situ stent using a dumbbell balloon as described in detail in Example 3 below. In that example, the dumbbell balloon permits filling of the entire aneurysmal sac with a fluid composition which is allowed to overflow the aneurysmal neck to form in situ a stent along the arterial wall by precipitation/polymerization of the fluid composition. Alternatively, the aneurysmal sac can be sufficiently filled with non-particulate agent via conventional techniques to inhibit blood flow therein and, subsequently, the dumbbell balloon is placed in the manner of Example 3. Delivery of a fluid composition then results in precipitation/polymerization of the fluid composition around the non-particulate agent. In addition, excess fluid composition is employed to permit this composition to overflow the aneurysmal neck to form in situ a stent along the arterial wall by precipitation/polymerization of the fluid composition.

Another method for non-endogenously isolating the parent artery wall from the systemic blood flow is the formation of in situ stent using a liquid permeable balloon as described in detail in Example 4 below. In that example, a fluid composition is delivered to the arterial walls of the parent artery by the liquid permeable balloon such that the exposed arterial walls are covered by the fluid composition. In situ solidification of the fluid composition results in the formation of a stent completely covering the exposed arterial walls of the parent artery.

Still further, a one-step process for both filling the aneurysmal sac and isolating the parent artery from the systemic blood flow is exemplified in Example 5 below. In this example, a dumbbell stent is employed which contains an open or porous structure. The open structure is aligned with the aneurysmal sac and then the tip of a microcatheter is fed through the open or porous structure into the aneurysmal sac. Fluid composition is delivered through the catheter tip in a manner such that the aneurysmal sac is filled with a sufficient amount of the fluid composition to inhibit blood flow into the aneurysm. Further filling is then conducted to allow overflow of the fluid composition at the neck of the aneurysm to encapsulate at least a portion of the open or porous structure of the stent both proximally and distally to the site of the aneurysm thereby isolating the exposed regions of the parent artery from blood flow both proximally and distally to the site of the aneurysm.

In each embodiment, the aneurysmal sac is filled to inhibit blood flow therethrough while the parent artery is non-endogenously isolated from the systemic blood flow, while still remaining patent. It is important to note that, in contrast to the prior art, isolation of the parent artery from the systemic blood flow in the methods of this invention does not rely solely upon formation of biological tissue to effect complete isolation of the parent artery. In this regard, growth of endogenous tissue, e.g, over a porous stent, to isolate the parent artery from blood circulation often occurs weeks after placement of the stent, if at all, during which time there can be regrowth of the aneurysmal sac or formation of a new aneurysm. Thus, for example, use of a porous or open stent, by itself, will not result in isolation of the parent artery from the blood flow until tissue growth envelops the pores of such stents.

Alternatively, the porous dumbbell stent described above can be replaced by a conventional porous stent described, for example, by Szikora, et al.[12] Still further, the stent employed can be non-biodegradable (e.g., made of tantalum filaments) or biodegradable. See, for example, Talia, et al.[16] The use of a biodegradable stent permits time for formation of tissue over the arterial endothelium while isolating the arterial wall of the parent artery from blood flow during formation of this tissue.

The particular catheters employed in the methods described herein are not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., Teflon™), silicone, etc.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc = | cubic centimeter |
| cSt = | centiStokes |
| DMSO = | dimethylsulfoxide |
| EVOH = | ethylene vinyl alcohol copolymer |
| g = | gram |
| mg = | milligram |
| mL = | milliliter |
| ppm = | parts per million |
| sec. = | seconds |
| μm = | micron |

Example 1

The purpose of this example is to demonstrate the preparation of two different polymer compositions useful in this invention.

Composition A

An EVOH polymer composition was prepared as follows:
(A) 8 g EVOH (48 mole percent ethylene);
(B) 30 g tantalum having an average particle size of about 3 μm (narrow size distribution); and
(C) 100 mL DMSO.

Each of the components of this composition were combined and the resulting mixture was mixed until homogenous.

In this composition, the average particle size of the contrast agent was prepared by fractionation wherein tantalum, having an average particle size of less than about 20 μm, was added to ethanol (absolute) in a clean environment. Agitation of the resulting suspension was followed by settling for approximately 40 sec. to permit the larger particles to settle faster. Removal of the upper portion of the ethanol followed by separation of the liquid from the particles results in a reduction of the particle size which is confirmed under a microscope (Nikon Alphaphot™). The process was repeated, as necessary until an average 3 μm particle size was reached.

Composition B approximately 15.1 weight % EVOH (48 mole percent ethylene)
18.2 weight % micronized tantalum
approximately 66.7 weight % DMSO
Viscosity=approximately 1100 cSt at 40° C.

In each case, after dissolution of the polymer at 50° C. in DMSO with stirring, micronized tantalum (average size 3 μm) was then added. The resulting composition was heated for about 5 minutes at 70° C. then shaken in a vortex mixer for approximately 20 minutes at room temperature to obtain a uniform suspension of the insoluble tantalum in the composition, then heated again for about 5 minutes at 70° C.

Example 2

The purpose of this example is to demonstrate the preparation of a prepolymer composition useful in this invention.

Specifically, a cyanoacrylate prepolymer composition was prepared by adding 800 mg of tantalum powder to 2 g n-butyl cyanoacrylate containing 100 ppm $SO_2$ as a stabilizer to yield a composition comprising 28% by weight of tantalum. The ingredients were mixed well, yielding a black suspension.

Example 3

Formation of In Situ Stent Via Dumbbell Balloon

The purpose of this example is to demonstrate procedures which can be used to inhibit systemic blood flow into an aneurysmal sac and isolation of the parent artery proximal and distal to the aneurysm from systemic blood flow by use of a balloon catheter apparatus to form an in situ stent. Generally, the balloon catheter apparatus is formed into a dumbbell shape at the vascular site near the aneurysmal sac. The fluid composition can then be injected around the narrow portion of the dumbbell to form an in situ stent.

As shown in FIG. 1, a single lumen catheter body (101) has first and second ends positioned so that when the first end (103) is located in the parent artery on one side of the aneurysmal sac, the second end (105) can be located in the parent artery on the opposite side of the aneurysmal sac. A first inner balloon (107) is bonded over the outside of the first end of the catheter body. A second inner balloon (109) is bonded over the outside of the second end of the catheter body. The catheter includes infusion or inflation holes (111) located in the first and second end regions of the catheter body covered by the first and second balloons to,allow for inflation and deflation of the inner balloons.

An outer balloon (113) is bonded over the outside of the catheter body, so that the two inner balloons are entrapped therein. As the two inner balloons are inflated, the outer balloon is pushed up at the first and second ends of the catheter body, creating a smooth and continuous dumbbell shaped outer surface of the outer balloon (113). When the apparatus, shown in FIG. 1, is located in the parent artery next to an aneurysm, the end bulges of the outer balloon (113) created by inflation of the inner balloons (107 and 109) are located in the parent artery on either side of the aneurysmal sac to keep the parent artery patent. The narrow portion of the dumbbell shaped outer balloon (113) is located in the parent artery adjacent the aneurysmal sac and provides a smooth and continuous surface for forming and in situ stent. Preferably, the narrow central portion of the outer balloon (113) also extends proximal and distal to the aneurysmal sac and creates a toroidal void into which the fluid composition can be delivered.

Once the inner balloons have been inflated, a second catheter can be used to insert a fluid composition into the aneurismal sac and into the space in the parent artery surrounding the narrow portion of the dumbbell shaped outer balloon, adjacent to, proximal to, and distal to the aneurysmal sac. Upon delivery, the fluid composition solidifies in the aneurysmal sac and in the annular space around the narrow portion of the outer balloon. After the fluid has solidified, the balloons can be deflated and the balloon catheter apparatus removed, leaving a in situ stent isolating the parent artery proximal and distal to the aneurysmal sac from the systemic blood flow. The in situ stent reinforces the wall of the vasculature at the location of and proximal and distal to the aneurysm and isolates the exposed portions of the parent artery from blood flow.

Figure 2:
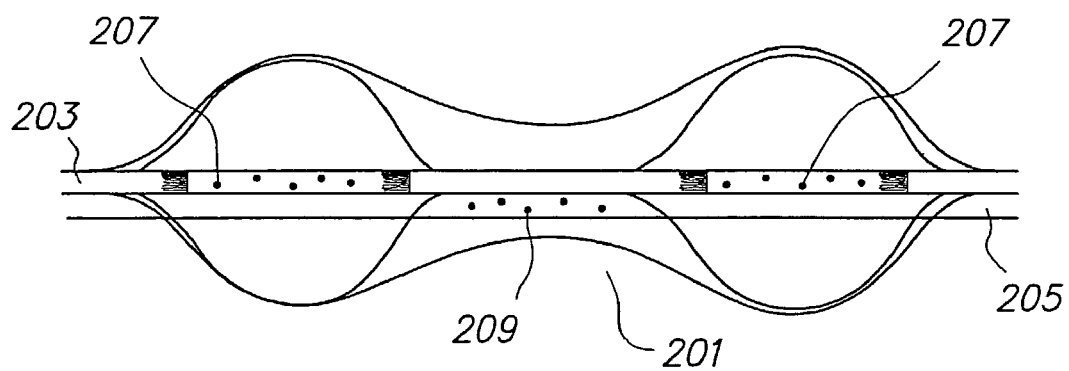
FIG. 2 is a schematic side view of an alternative embodiment of the balloon catheter of FIG. 1 with a double lumen.

As an alternative embodiment of the above example, the single lumen balloon catheter can be replaced with a double lumen catheter (201) shown in FIG. 2, where a first lumen (203) provides for the infusion and inflation of the two inner balloons and a second lumen (205) provides for the infusion and inflation of the outer balloon. This double lumen catheter embodiment provides for independent control of the inner and outer balloon. Inner balloon infusion holes (207) provide for control of the inner balloons. Outer balloon infusion holes (209) provide for control of the outer balloons.

According to another alternative embodiment, the dumbbell shaped balloon structure may be replaced with a substantially cylindrical or constant diameter balloon which has been under inflated. The balloon can act as a trampoline allowing the fluid composition to push the balloon inward filling a space formed between the balloon and the wall of the parent artery with the fluid composition. Upon solidification, the balloon is deflated and removed leaving an in situ stent.

Example 4

Formation of In Situ Stent Via Permeable Balloon

The purpose of this example is to demonstrate procedures which can be used to inhibit systemic blood flow into an aneurysmal sac by filling the aneurysmal sac with a fluid composition and/or non-particulate agents, and then isolating the parent artery proximal and distal to the aneurysm by forming an in situ stent near the vascular site of the aneurysm with the use of a liquid permeable balloon.

First, the methods described herein employ conventional catheter techniques to fill the aneurysmal sac with a fluid composition and/or non-particulate agents, as described above.

Second, the methods described herein employ conventional endovascular catheter techniques to direct a liquid permeable balloon catheter to the vascular site of the aneurysm. The liquid permeable balloon catheter preferably includes an inner impermeable saline filled balloon and an outer permeable balloon positioned coaxially around the inner balloon. Once the liquid permeable balloon catheter is placed at the selected vascular site, the inner balloon is inflated with saline to locate and hold the balloon at the vascular site. Positive pressure is then created within the outer balloon by delivery of the fluid composition to the outer balloon. The outer permeable balloon inflates and intimately contacts the arterial wall of the parent artery. The positive pressure is preferably generated in the form of injecting a fluid composition comprising a water insoluble biocompatible polymer, a biocompatible solvent and a water insoluble contrast agent into the balloon. Once inflated, the outer balloon is maintained inflated under physiological conditions for a period of time (e.g., one to ten minutes) to permit a portion of the fluid composition to permeate through holes in the outer permeable balloon and contact the arterial wall of the parent artery. The outer permeable balloon preferably is formed with laser drilled holes arranged in a pattern selected to achieve the desired delivery pattern of the fluid composition.

When the fluid composition is introduced in vivo at the vascular site through the permeable balloon, the biocompatible solvent diffuses rapidly into the body fluid and a solid, non-migratory precipitate or solid mass forms which precipitate is the water insoluble polymer and water insoluble contrast agent encapsulated therein. This precipitate preferably covers all of the arterial wall of the parent artery which is in contact with the balloon.

When a prepolymeric composition is introduced in vivo through the fluid permeable balloon, the prepolymer rapidly polymerizes in situ (preferably in less than 15 minutes and more preferably in less than 5 minutes) and a solid non-migratory mass forms against the arterial wall of the parent artery which is in contact with the balloon which mass is the water insoluble polymer and contrast agent encapsulated therein.

When an adhesive polymer is employed (i.e., cyanoacrylate) care should be taken to prevent adherence of the cured polymer to the balloon.

In either case, a solid non-migratory mass forms an in situ stent in the vascular site so that the in situ stent isolates the parent artery of the aneurysm proximal and distal to the aneurysm from the systemic blood flow. The size and thickness of the in situ stent formed relate directly to the size and arrangement of holes of the balloon selected as well as the extent and duration of positive pressure maintained on the inflated balloon. Such factors are well within the skill of the art. Preferably, the in situ formed stent thicknesses formed by the methods of this invention range from about 0.05 mm to about 1 mm and, more preferably, from about 0.05 mm to about 0.5 mm.

The in situ stent provides the advantage of preventing the occurrence of new aneurysms adjacent the treated aneurysm by protecting the walls of the parent artery proximal and distal to the aneurysm being treated. The in situ stent may also provide a surface for endothelial tissue in growth at the aneurysm site and proximal and distal to the aneurysm. The endothelial tissue growth may provide added strengthening of the parent artery and blood compatibility.

Example 5

Formation of In Situ Stent Via Dumbbell-Shaped Mechanical Stent

The purpose of this example is to demonstrate procedures for the inhibition of systemic blood flow into an aneurysmal sac by filling the aneurysmal sac with a fluid composition and/or non-particulate agents, and isolating the parent artery proximal and distal to the aneurysm by forming an in situ stent near the vascular site of the aneurysm with the use of a dumbbell shaped mechanical stent.

Figure 3:
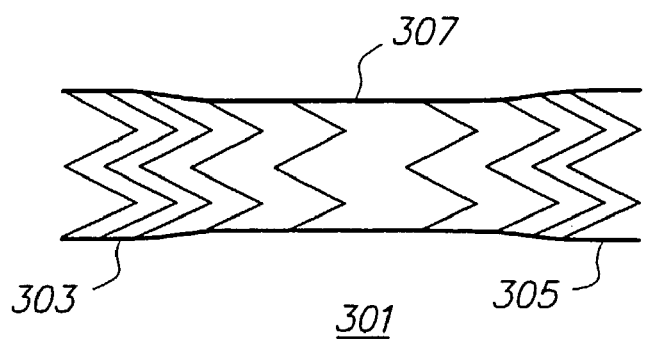
FIG. 3 is a schematic side view of a stent for use in a method of treating an aneurysm according to the present invention.

According to this embodiment of the invention, a dumbbell-shaped mechanical stent (301), as shown in FIG. 3, is placed in the parent artery adjacent an aneurysmal sac. The mechanical stent has two rigid end segments (303, 305) which can be expanded against the sides of the parent artery in a known manner, e.g., balloon or self expanding, when the stent is placed near an aneurysm. The mechanical stent also has a flexible region (307) or open mesh or other open structure located in between the two rigid end segments (303, 305). The flexible region (307) of the mechanical stent allows for increased ease of manipulation or trackability of the stent through the vasculature as the stent is directed to the site of the aneurysm. This flexible region also minimizes the amount of blood vessel straightening that can occur as the stent is directed to the site of the aneurysm. The structure of the stent (301) may be formed by a mesh, screen, laser cut tube, lattice, coil, wires, or any other known stent structure.

The diameter of the flexible central region (307) of the mechanical stent is less than the diameter of the rigid end segments (303, 305) of the stent. The stent is preferably delivered and deployed by a dumbbell shaped balloon catheter having a central section with a smaller diameter than end regions. The smaller diameter of the flexible central region (307) of the stent and the corresponding shape of the dumbbell shaped deployment balloon ensures that the flexible region of the mechanical stent does not apply any outward distension force to the blood vessel wall of the parent artery after its deployment at the location of the aneurysm.

Figure 4:
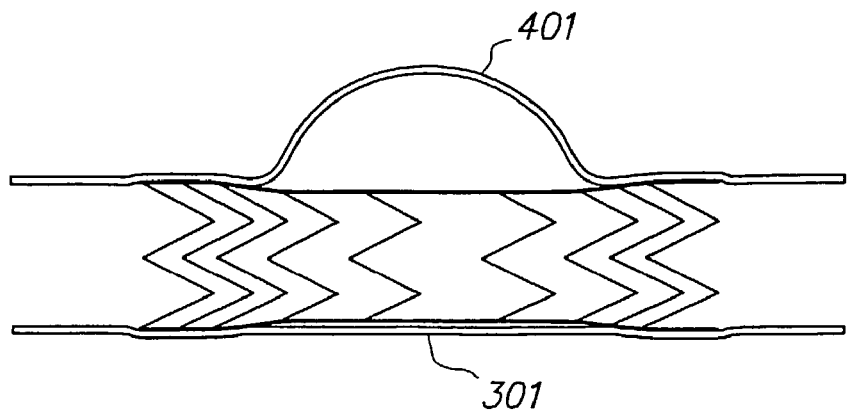
FIG. 4 is a schematic side view of the stent of FIG. 3 positioned in the parent artery near an aneurysm.

Upon deployment of the mechanical stent, the more rigid end segments secure the stent in place and prevent migration by applying radial distension forces to the walls of the parent artery distal and proximal the aneurysm. As shown in FIG. 4, the smaller diameter central region (307) prevents unnecessary pressure from being exerted against the weakened section of the parent artery near the aneurysmal sac (401). Even in the case of over-expansion of the stent during deployment, as often happens in clinical practice, the central region will not apply any radial force on the weakened portion of the parent vessel.

Figure 5:
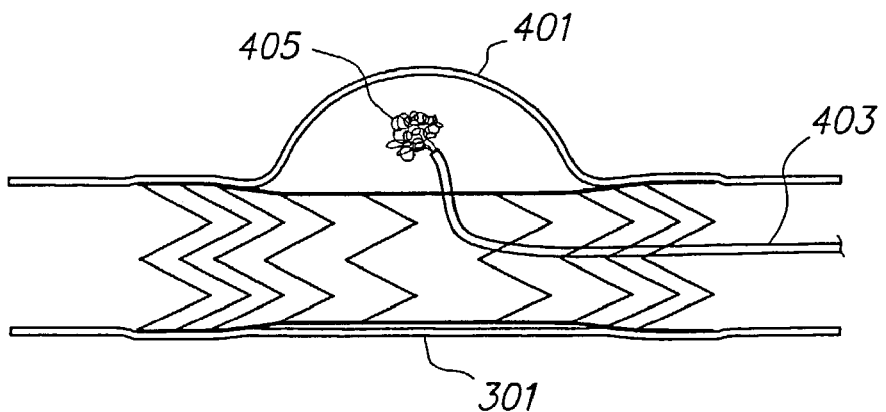
FIG. 5 is a schematic side view of the stent of FIG. 3 with the fluid composition being delivered to the aneurysm for treatment of the aneurysm.
Figure 6:
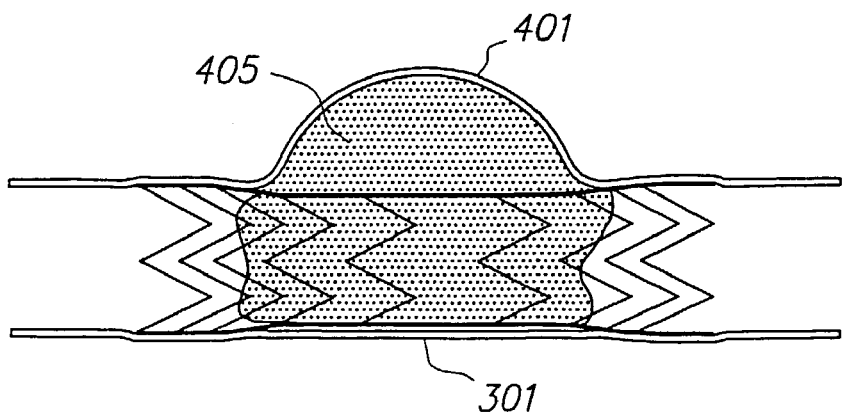
FIG. 6 is a schematic side view of the stent of FIG. 3 with the fluid composition filling the aneurysmal sac and the space around the stent's outer surface between the stent and the diseased wall.

In FIG. 5, the fluid composition (405) is delivered to the aneurysm sac and the annular space surrounding the central region of the mechanical stent by a catheter (403) which may be fed through the open mesh of the central region of the stent. As shown in FIG. 6, the fluid flows into the aneurysmal sac, filling the sac and the space around the stent's outer surface between the stent and the diseased arterial wall. The smaller diameter of the flexible central region of the mechanical stent allows for the formation of an in situ polymer stent around the parent artery in the region of the smaller diameter, flexible region of the mechanical stent. The in situ stent may reinforce the wall of the vasculature at the location of and proximal and distal to the aneurysm. The smaller diameter of the flexible central region also allows the polymer material to completely isolate a neck of the aneurysm sac and prevent aneurysm regrowth at the neck.

From the foregoing description, various modifications and changes in the composition and method will occur to those skilled in the art. All such modifications coming within the scope of the appended claims are intended to be included therein.

What is claimed is:

1. A method for treating an aneurysm in a mammalian patient which method comprises:
    (a) identifying the vascular site of an aneurysm in a mammalian patient wherein said aneurysm comprises an aneurysmal sac formed from the vascular wall of a parent artery and further wherein said aneurysmal sac participates in the systemic blood flow of said patient;
    (b) inhibiting systemic blood flow into said aneurysmal sac by filling at least a portion of said sac with a fluid composition and optionally a non-particulate agent or plurality of said agents; and
    (c) non-endogenously isolating the parent artery proximal and distal to said aneurysm from systemic blood flow wherein the fluid composition comprises a biocompatible polymer, a biocompatible contrast agent, and a biocompatible solvent which solubilizes the biocompatible polymer having a viscosity of at least 150 cSt at 40° C.

2. The method of claim 1, wherein the non-particulate agent or plurality of non-particulate agents comprise metallic coils.

3. The method of claim 2, wherein the metallic coils are platinum coils.

4. The method of claim 1, wherein the fluid composition comprises a biocompatible polymer at a concentration of from about 2 to 50 weight percent; a biocompatible contrast agent at a concentration of from about 10 to about 40 weight percent; and a biocompatible solvent from about 10 to 88 weight percent wherein the weight percents of the biocompatible polymer, contrast agent and biocompatible solvent are based on total weight of the complete composition.

5. The method of claim 1, wherein isolation of the parent artery proximal and distal to said aneurysm from systemic blood flow is accomplished by placement of a stent adjacent to the aneurysmal sac which stent extends in both the proximal and distal directions of the parent artery beyond the aneurysal sac and isolates blood flow to the arterial walls of the parent artery overlayed by the stent.

* * * * *